United States Patent
Thorley et al.

[19]

[11] Patent Number: 6,083,199
[45] Date of Patent: Jul. 4, 2000

[54] RETRACTABLE SYRINGE

[76] Inventors: Craig Stephen Thorley, 275 Paterson Road, Bolwarra, New South Wales 2320; Joseph Hermes Kaal, 84 Swan Street, Morpeth, New South Wales 2321, both of Australia

[21] Appl. No.: 09/158,633

[22] Filed: Sep. 22, 1998

[30] Foreign Application Priority Data

Sep. 23, 1997 [AU] Australia ................................. PO9406

[51] Int. Cl.[7] .................................................. A61M 5/00
[52] U.S. Cl. ........................................... 604/110; 604/195
[58] Field of Search ................................... 604/110, 187, 604/194, 195, 196, 197, 198, 218, 220

[56] References Cited

U.S. PATENT DOCUMENTS

| | | | |
|---|---|---|---|
| 4,946,446 | 8/1990 | Vadher | 604/198 |
| 5,279,579 | 1/1994 | D'Amico | 604/192 |
| 5,292,314 | 3/1994 | D'Alessio et al. | 604/198 |
| 5,338,311 | 8/1994 | Mahurkar | 604/195 |
| 5,346,480 | 9/1994 | Hess et al. | 604/197 |
| 5,411,487 | 5/1995 | Castagna | 604/198 |
| 5,429,613 | 7/1995 | D'Amico | 604/198 |
| 5,514,097 | 5/1996 | Knauer | 604/136 |
| 5,531,694 | 7/1996 | Clemes et al. | 604/110 |
| 5,562,623 | 10/1996 | Shonfeld et al. | 604/110 |
| 5,643,222 | 7/1997 | Mahurkar | 604/195 |
| 5,762,634 | 6/1998 | Davis | 604/195 |
| 5,879,338 | 3/1999 | Mahurkar | 604/195 |

*Primary Examiner*—Corrine McDermott
*Attorney, Agent, or Firm*—Ladas & Parry

[57] ABSTRACT

A single use retractable syringe (1) comprises a hollow barrel (2), a needle (3) engaged with a first end (4) of the hollow barrel (2) and a plunger (5) slideably disposed in the hollow barrel (2). Corresponding interlocking portions (6,7) are provided on the plunger (5) and needle (3) and are engageable only when radially aligned. The syringe (1) is provided with means for rotating the plunger (5) relative to the needle (3) from an orientation where the corresponding interlocking portions (6,7) are radially non-aligned on an initial depression of the plunger (5) toward the hollow barrel first end (4) to expel air to an orientation where the corresponding interlocking portions (6,7) are radially aligned on a subsequent depression of the plunger (5) to dispense fluid from the hollow barrel (2), thereby enabling the corresponding interlocking portions (6,7) to engage and retract the needle (3) into the hollow barrel (2) on a subsequent retraction of the plunger (5) away from the first end (4) following use.

6 Claims, 11 Drawing Sheets

RETRACTABLE SYRINGE

TECHNICAL FIELD

The present invention relates to medical syringes, and in particular relates to a single use retractable syringe.

BACKGROUND OF THE INVENTION

Typical currently available syringes present a health hazard after use. The needle of the syringe remains protruding from the barrel after use, and if a protective cap is not fitted to the used needle, or such cap is dislodged, the needle can readily puncture the skin of anyone who handles or accidentally treads on the syringe. As several deadly diseases such as human immunodeficiency virus (HIV) and hepatitis C are transmitted by infected bodily fluids which may remain in the needle following a previous use, puncture of the skin by a used syringe can result in the transmission of such deadly diseases.

Transmission of such diseases is a particular problem with intravenous drug users who may attempt to re-use an infected syringe to inject drugs.

Whilst single use needles have been proposed which retract the needle into the hollow barrel after use, such needles are typically cumbersome to operate.

OBJECT OF THE INVENTION

It is the object of the present invention to overcome or substantially ameliorate the above disadvantages.

SUMMARY OF THE INVENTION

There is disclosed herein a single use retractable syringe comprising:

a hollow barrel, a needle engaged with a first end of said hollow barrel, a plunger slideably disposed in said hollow barrel, corresponding interlocking portions provided on each of said plunger and said needle, said corresponding interlocking portions being engageable only when radially aligned, and means for rotating said plunger relative to said needle from an orientation where said corresponding interlocking portions are radially non-aligned on an initial depression of said plunger toward said first end to expel air from said hollow barrel in preparation for intake of fluid into said hollow barrel during an initial retraction of said plunger away from said first end, to an orientation where said corresponding interlocking portions are radially aligned on a subsequent depression of said plunger to dispense said fluid from said hollow barrel, thereby enabling said corresponding interlocking portions to engage and retract said needle into said hollow barrel on a subsequent retraction of said plunger away from said first end following use.

Typically, said means for rotating said plunger includes a projection mounted on said hollow barrel and associated with first and second slots provided on said plunger, said projection engaging said first slot prior to use, said engagement of said projection and said first slot radially non-aligning said corresponding interlocking portions upon said initial depression of said plunger, said first and second slots communicating such that upon an initial retraction following said initial depression and said subsequent depression of said plunger, said first slot guides said projection into engagement with said second slot whilst rotating said plunger such that, on said subsequent depression of said plunger, said corresponding interlocking members are radially aligned so as to be engageable.

Preferably said second slot extends substantially straight parallel to a longitudinal axis of said plunger, said first slot extending substantially straight parallel to said second slot from an end of said plunger distal to said hollow barrel first end to partway along said plunger where said first slot deviates circumferentially to intersect with said second slot.

Preferably said projection is formed on a cap mounted on a second end of said hollow barrel opposed to said first end.

Preferably said means for rotating said plunger is adapted to rotate said plunger through approximately 90°.

The syringe may further include means for automatically blocking off said first end of said hollow barrel upon retraction of said needle into said hollow barrel.

Preferably said means for automatically blocking off said first end of said hollow barrel comprises a clip having a protruding portion, said protruding portion abutting said needle and said clip being biased such that, on retraction of said needle into said hollow barrel, said protruding portion moves to block off an aperture vacated by said retracting needle.

Preferably said plunger is spring biased to a retracted position.

BRIEF DESCRIPTION OF THE DRAWINGS

Preferred forms of the present invention will now be described by way of example with reference to the accompanying drawings wherein.

DETAILED DESCRIPTION OF THE PREFERRED EMBODIMENTS

The retractable syringe 1 of the first preferred embodiment as depicted in FIGS. 1 to 17 comprises a hollow barrel 2, a needle 3 engaged with a first end 4 of the hollow barrel 2 and a plunger 5 slideably disposed in the hollow barrel 2. The plunger 5 is engageable with the needle 3 so as to enable disengaging of the needle 3 from the hollow barrel first end 4 as the plunger is retracted away from the hollow barrel first end 4 following use dispensing fluid from the hollow body 4 through the needle 3. Retraction of the plunger 5 with which the needle 3 is engaged draws the needle 3 into the hollow barrel 2, thus preventing accidental puncture of the skin with the used needle 3 or re-use by intravenous drug users.

Figure 1:
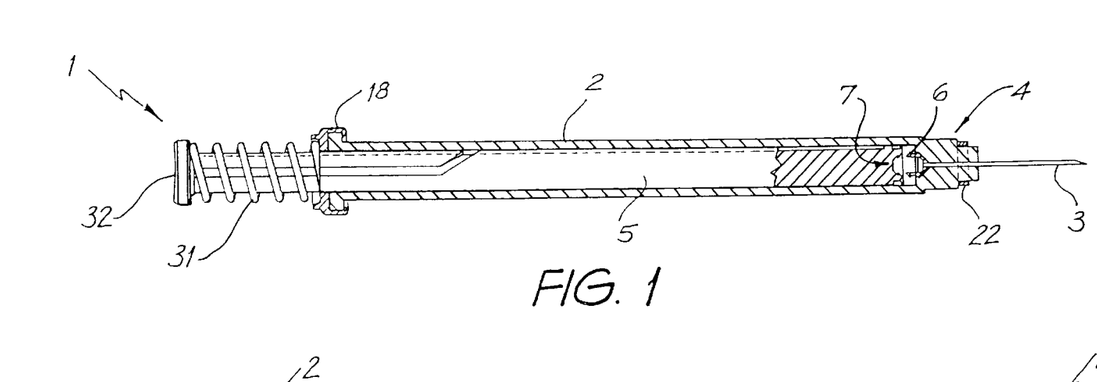
FIG. 1 is a schematic cross-sectional elevation view of the retractable syringe of a first preferred embodiment.
Figures 2, 3, 4:
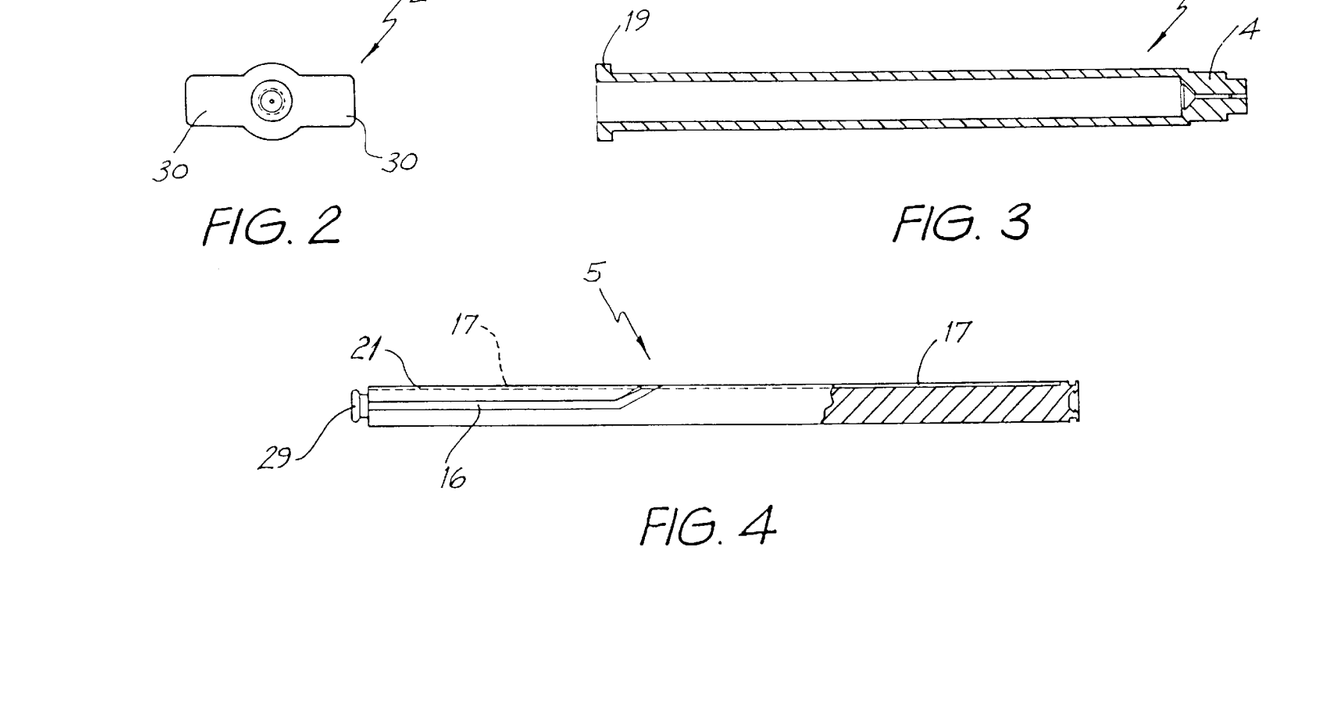
FIG. 2 is an end elevation view of the hollow barrel of the retractable syringe of FIG. 1.
FIG. 3 is a cross-sectional elevation view of the hollow barrel of FIG. 2.
FIG. 4 is a cross-sectional elevation view of the plunger of the retractable syringe of FIG. 1.
Figure 5:
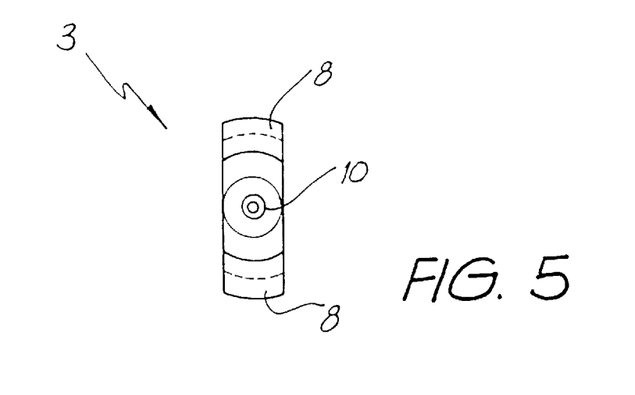
FIG. 5 is an end view of the needle of the retractable syringe of FIG. 1.
Figure 6:
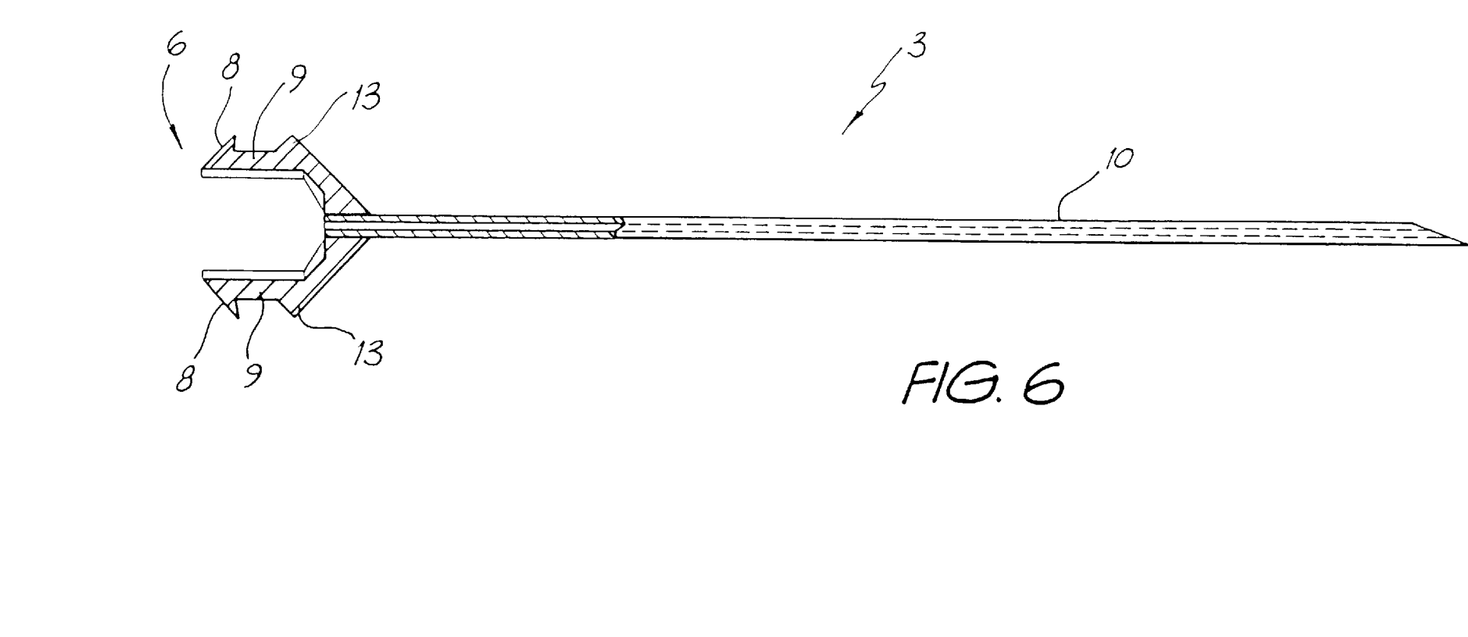
FIG. 6 is an elevation view of the needle of FIG. 5.

In use the plunger 5 is initially depressed toward the hollow barrel first end 4 to expel any air from the hollow barrel 2, at the end of this initial depression the plunger 5 does not engage the needle 3, so that the needle 3 remains engaged with the hollow barrel first end 4. Fluid to be injected, typically a serum, is then drawn into the hollow barrel 2 through the needle 3 in the usual manner as the plunger 5 is initially retracted. On a subsequent depression of the plunger 5 to dispense the fluid from the hollow barrel 2 through the needle 3, the plunger 5 engages the used needle 3, with a subsequent retraction of the plunger 5 disengaging the needle 3 from the hollow barrel first end 4 and retracting the needle 3 into the hollow barrel 2 as outlined above. FIG. 1 depicts the syringe 1 with the plunger 5 in the subsequent depression stroke immediately prior to engaging with the needle 3.

The needle 3 and plunger 5 are provided with corresponding interlocking portions 6, 7 by which the needle 3 and plunger 5 are able to engage. The needle interlocking portions 6, best depicted in FIGS. 5 and 6, comprise barbs 8 provided at the end of arms 9 which extend parallel to the needle shaft 10 at opposing sides thereof.

Figure 7:
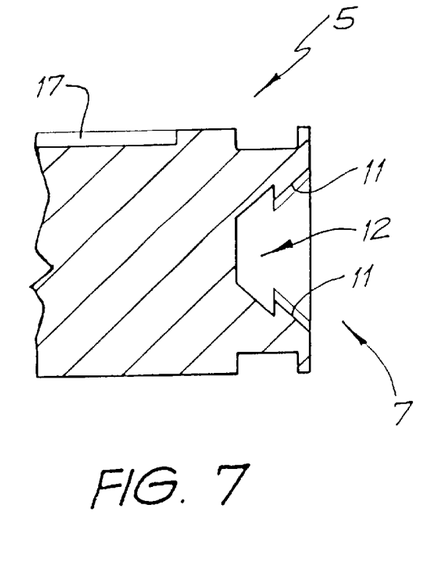
FIG. 7 is a fragmentary cross-sectional elevation view of the end of the plunger of FIG. 4.
Figure 8:
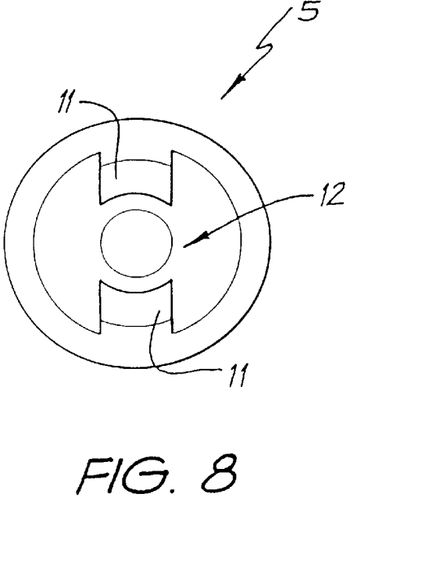
FIG. 8 is an end elevation view of the plunger of FIG. 4.
Figure 9:
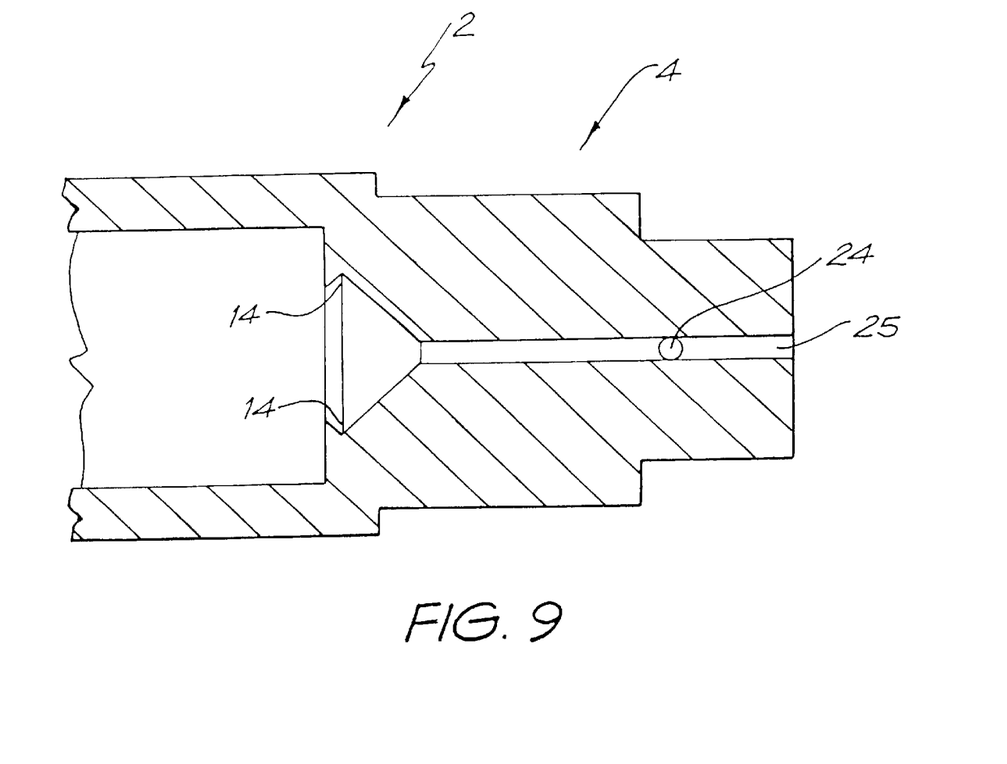
FIG. 9 is a fragmentary cross-sectional elevation view of the first end of the hollow barrel of FIG. 3.
Figure 11:
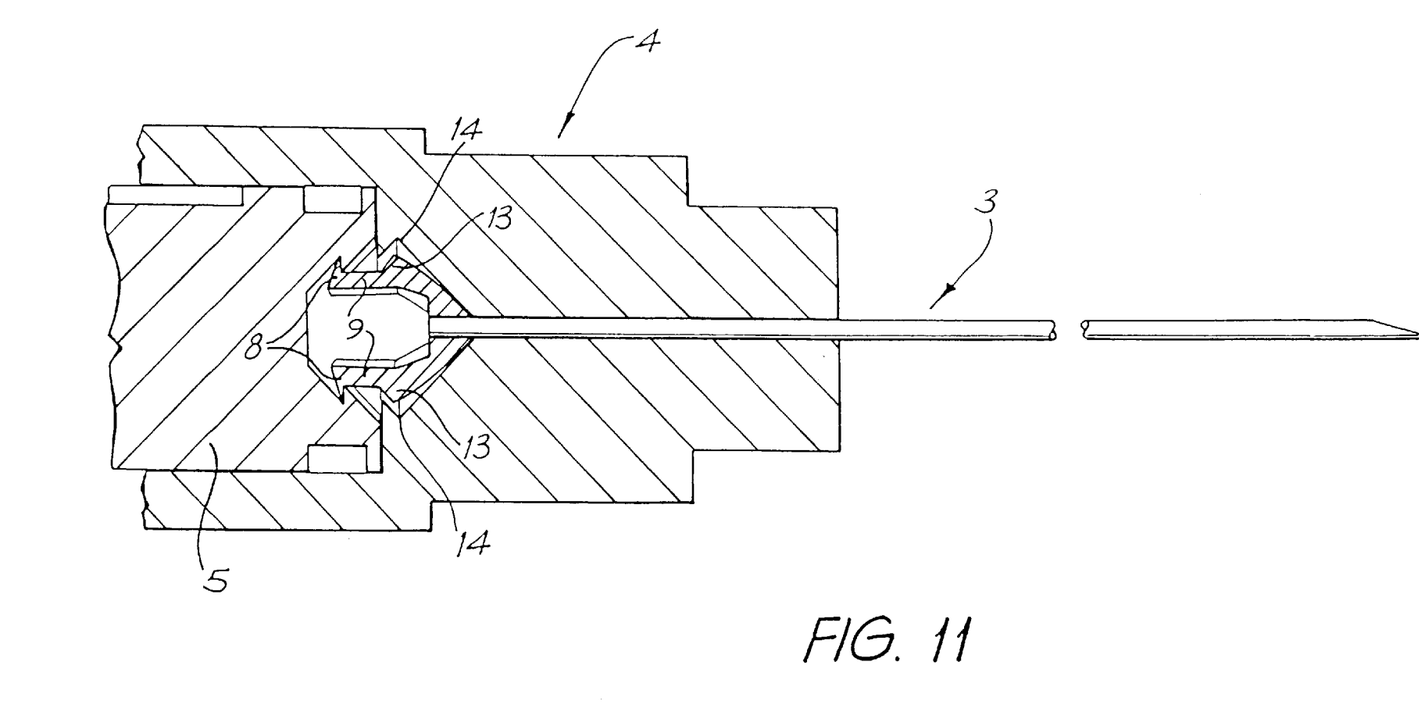
FIG. 11 is a fragmentary cross-sectional elevation view depicting engagement of the plunger with the needle in the first end of the hollow barrel.
Figure 12:
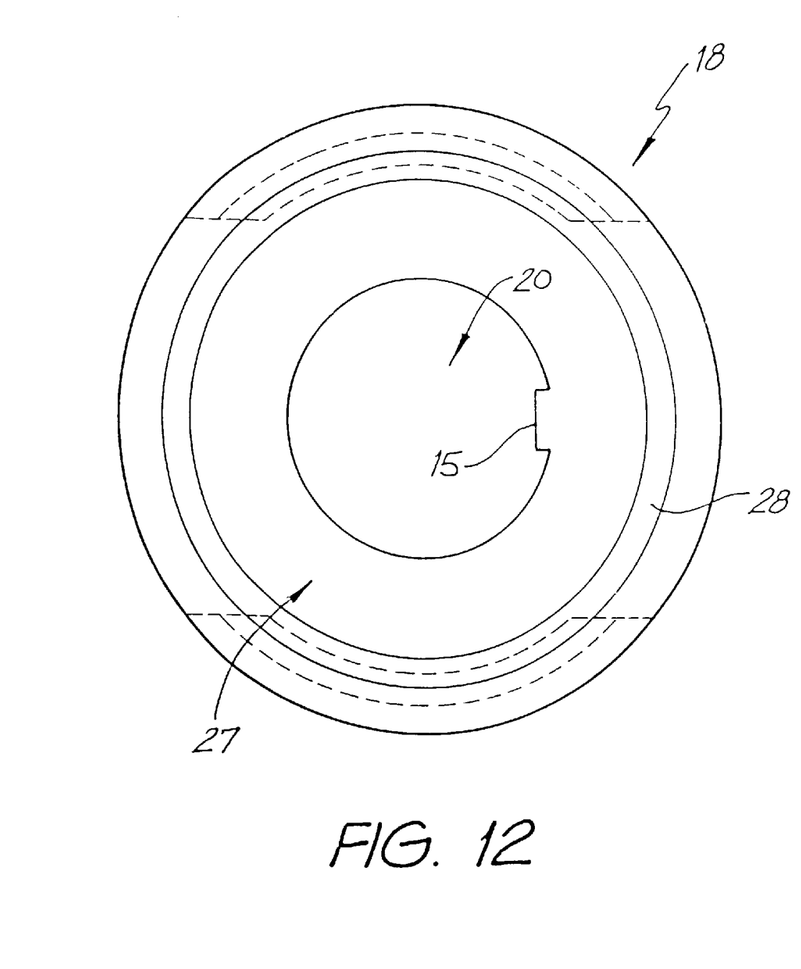
FIG. 12 is an end elevation view of the cap of the retractable syringe of FIG. 1.
Figure 13:
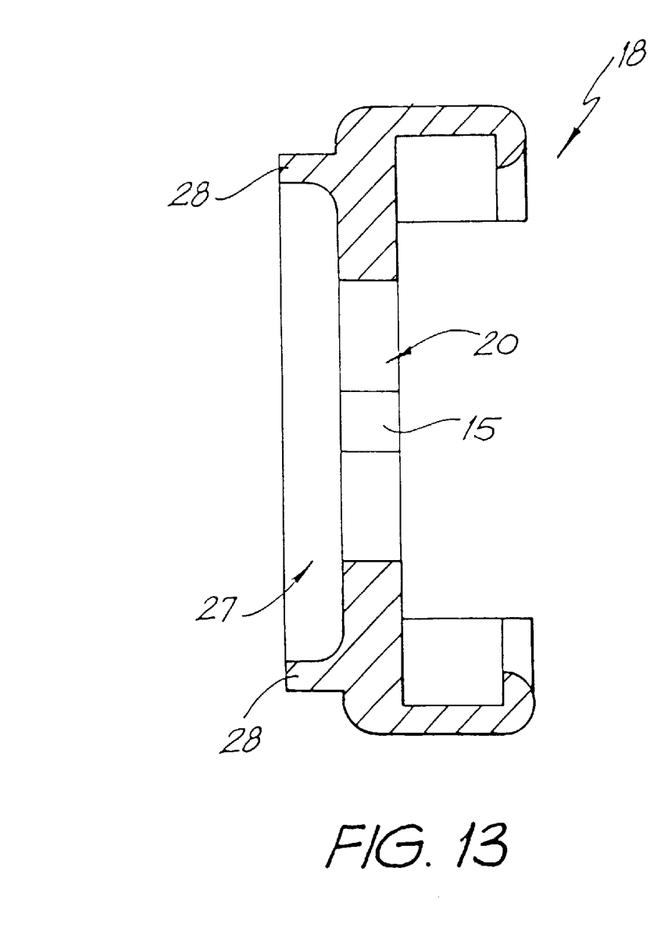
FIG. 13 is a cross-sectional elevation view of the cap of FIG. 12.

The plunger interlocking portions 7, best depicted in FIGS. 7 and 8, comprise tabs 11 which project inwardly from opposing sides of a recess 12 provided in the end of the plunger 5. When the corresponding interlocking portions 6,7 are radially aligned and the plunger 5 is depressed toward the hollow barrel first end 4, the needle barbs 8 contact the outward facing surfaces of the plunger tabs 11. The angled contacting faces of the barbs 8 and tabs 11 and continued axial movement of the plunger 5 create a radial force on the barbs 8 which tends to deflect the needle arms 9 inwardly, thereby allowing the barbs 8 to ride up over the tabs 11 and into the recess 12. The subsequent outward restoring deflection of the arms 9 locks the barbs 8 behind the tabs 11 in the recess 12 as shown in FIG. 11. The needle 3 and plunger 5 are thus engaged. As the interlocking portions 6, 7 of both the needle 3 and plunger 5 are radially opposed, contact of the needle 3 and plunger 5 in other than a radially aligned relationship will result in the interlocking portions 6, 7 not engaging.

Figure 10:
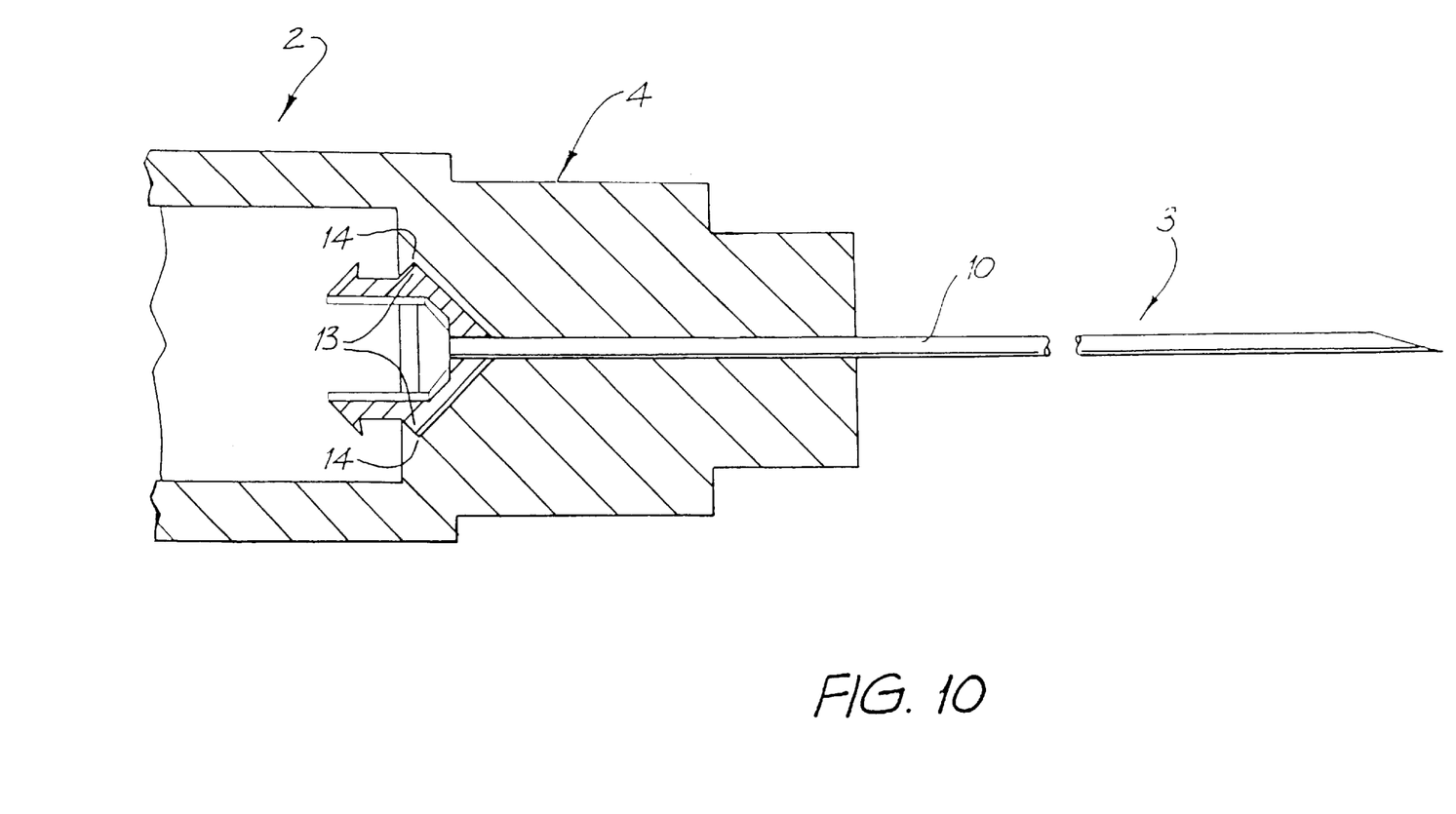
FIG. 10 is a fragmentary cross-sectional elevation view depicting engagement of the needle with the first end of the hollow barrel.

Prior to being disengaged by the plunger 5, the needle 3 is engaged with the hollow barrel first end 4 by means of triangular prism type projections 13 provided toward the base of each of the opposing arms 9 of the needle 3, as shown in FIG. 10. The triangular prism type projections 13 are regularly engaged in corresponding grooves 14 provided in the hollow barrel first end 4. Once the needle 3 is engaged with the plunger 5, retraction of the plunger 5 causes the angled side of the triangular prism type projections 13 to ride up over the angled side of the grooves 14 so as to disengage the needle 3 and hollow barrel first end 4. The disengaging of the projections 13 from the grooves 14 is associated with some deflection of the needle arms 9, but not sufficient to disengage the needle barbs 8 from the plunger tabs 11. As will be appreciated from the above, the needle arms 9 should be made from a resilient material.

To provide for the radial non-alignment of the corresponding interlocking portions 6, 7 on the initial depression of the plunger 5 to expel air and for radial alignment on the subsequent depression of the plunger 5 to dispense fluid, a projection 15 is associated with first and second slots 16, 17 provided on the plunger 5. The projection 15 is provided on a cap 18, depicted in FIGS. 12 and 13, which is mounted onto the second end 19 of the hollow barrel 2 during assembly of the syringe 1. The projection 15 extends radially inwardly from the edge of the hole 20 in the cap 18 through which the plunger 5 slides. The cap 18 is fitted such that the projection initially engages the first slot 16 prior to use, with engagement of the projection 15 and first slot 16 radially non-aligning the corresponding interlocking portions 6, 7 such that they will not engage on initial depression of the plunger 5 to expel air from the hollow barrel.

The first slot 16 longitudinally extends from the second end 21 of the plunger to part way along the plunger's length, where the first slot 16 deviates circumferentially to meet the second slot 17. As a result of the deviation of the first slot 16 as the plunger 5 is retracted to receive fluid into the hollow barrel 2 directly following its initial depression, the projection 15 will be guided from the first slot 16 through the deviation and into the second slot 17. As the projection 15 is fixed, this will result in the plunger 5 being rotated through 90° so that the corresponding interlocking portions 6, 7 align. The second slot 17 longitudinally extends from the second end of the plunger 5 to adjacent the first end 21 of the plunger. On the subsequent depression of the plunger 5 to dispense fluid, the corresponding interlocking portions 6,7 will engage at the end of the stroke, enabling disengagement of the needle 3 from the hollow barrel first end 4 and retraction of the needle 3 into the hollow barrel 2 as the plunger 5 is subsequently retracted. Whilst the slots 16, 17 extend parallel to the longitudinal axis of the plunger 5, other configurations will also be suitable so long as the interlocking portions 6, 7 will not engage at the end of the initial plunger 5 depression but will engage at the end of the subsequent plunger 5 depression.

Figure 15:
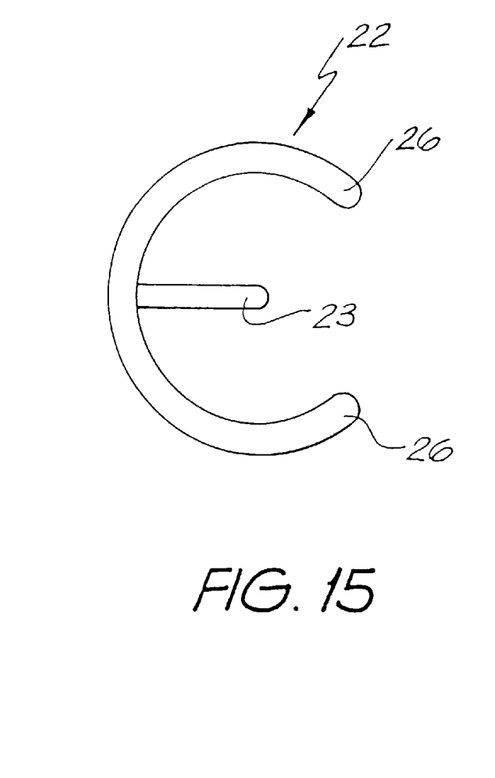
FIG. 15 is an end elevation view of the clip of FIG. 14.
Figure 16:
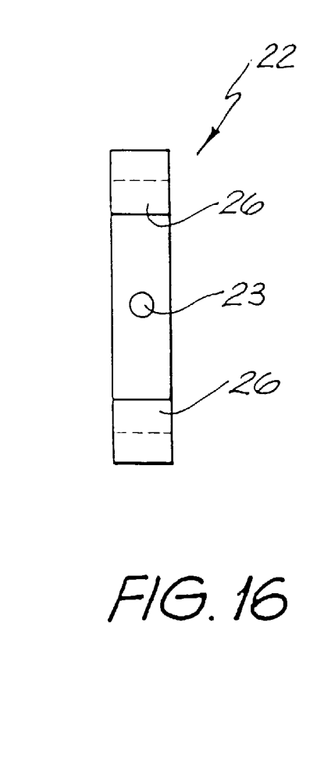
FIG. 16 is an elevation view of the clip of FIG. 15.

The retractable syringe 1 of the preferred embodiment includes means for automatically blocking off the first end 4 of the hollow barrel 2 upon retraction of the needle 3 into the hollow barrel 2. Here the blocking off means comprises a clip 22, as depicted in FIGS. 15 and 16, having a protruding portion 23. The clip 22 is of the general form of a circlip with the protruding portion 23 being in the form of a central pin 23 projecting radially toward the centre of the clip 22. The clip 22 is mounted on the hollow barrel first end 4, with the central pin 23 extending into a corresponding hole 24 extending radially through the hollow barrel first end 4 to communicate with a central longitudinally extending aperture 25 through which the needle shaft 10 projects.

Figure 14:
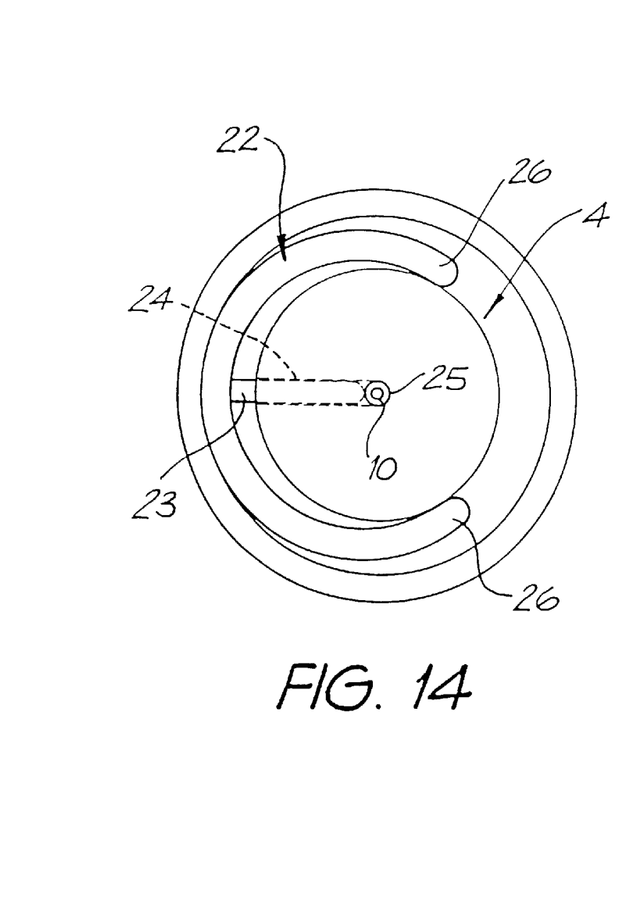
FIG. 14 is an end elevation view depicting a clip mounted on the first end of the hollow barrel abutting the needle.

With the needle 3 engaged with the hollow barrel first end 4, the free end of the central pin 23 abuts the needle 3, as depicted in FIG. 14. At this position, the ends 26 of the circlip type portion of the clip 22 extend beyond the diametrical centre of the hollow barrel first end 4 on which it is mounted, such that the inwardly directed ends 26 tend to draw the clip 22 further onto the hollow barrel first end 4, thereby biasing the central pin 23 against the needle 3.

When the needle 3 is retracted into the hollow barrel 2, the biasing action forces the clip 22 further onto the hollow barrel first end 4, thereby moving the central pin 23 deeper into the radially extending hole 24 and across the longitudinally extending aperture 25 to block off the same. The pin 23 preferably has a sealing fit such that the cavity of the hollow barrel 2 is sealed from the external environment, preventing the escape of any fluids and contaminants therein. A loose fit, however, will be sufficient to block off the hollow barrel first end 4 and thereby prevent the used needle 3 from being projected back out from the hollow barrel first end 4 by further depression of the plunger 5. Rather than project through a hole 24, an alternative clip may be provided where a protruding portion extends over the end of the longitudinally extending aperture 25 to block the same. A removable clip (not shown) will also typically be provided over the end of the aperture 25 and needle 3 to protect the need prior to use.

Figure 17:
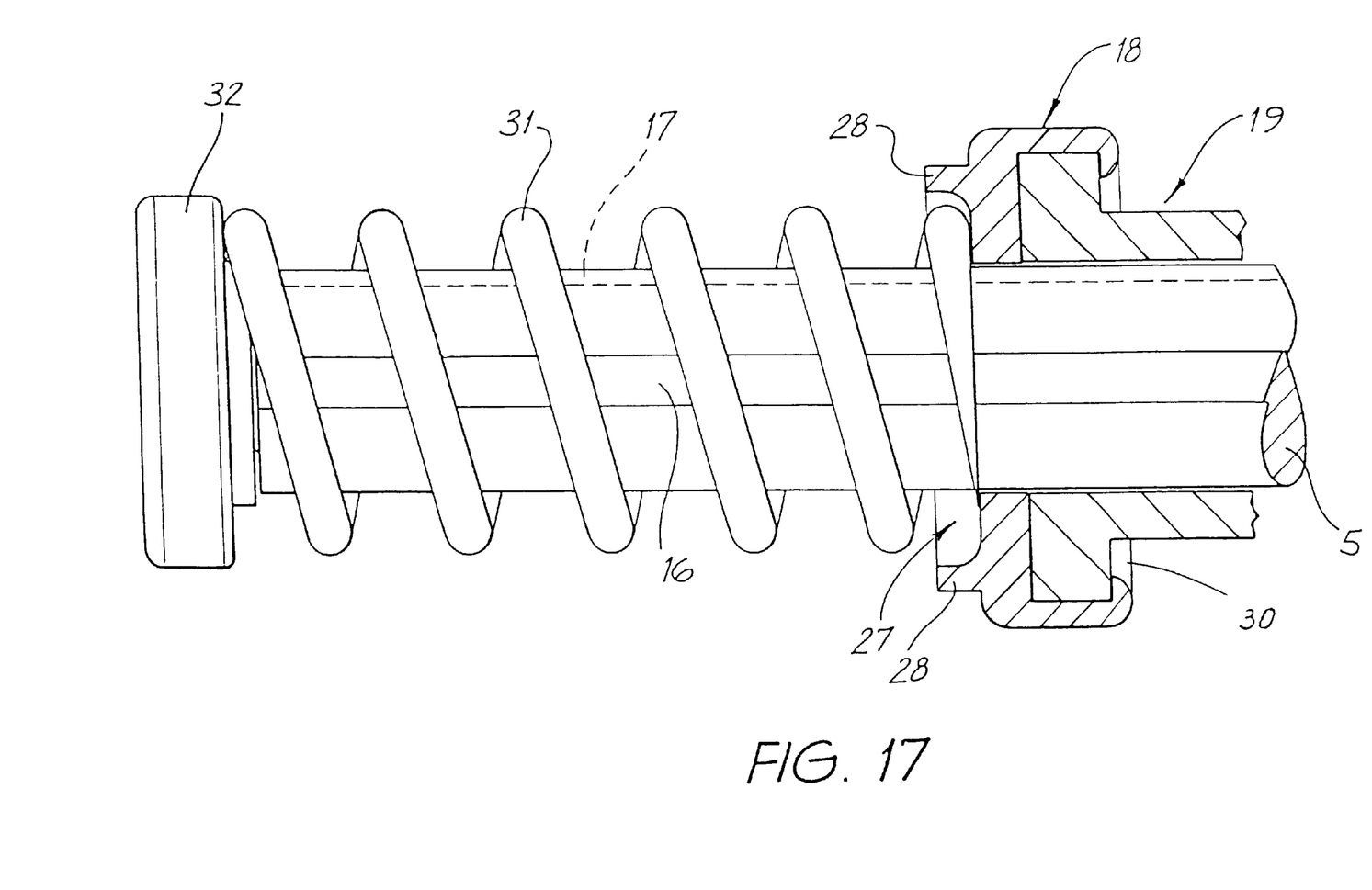
FIG. 17 is a fragmentary schematic elevation view depicting the mounting of the helical spring.

The plunger 5 is preferably spring biased toward a retracted position away from the hollow barrel first end 4. To achieve the spring bias, a helical spring 31 is mounted on the cap 18 positioned on the hollow barrel second end 19, as depicted in FIG. 17. The first end coils of the spring are disposed within a recess 27 defined by a circumferential flange 28 on the end of the cap 18. The helical spring 31 receives the plunger 5 therethrough, and the second end of the helical spring 31 is fixed longitudinally with respect to the plunger 5 by means of a thumb rest segment 32 which is snapped onto the projection 29 provided at the end of the plunger 5. The helical spring 31 is thus restrained between the cap 18 and thumb rest segment 32

The thumb rest segment 32 is used to depress the plunger 5 by the thumb of the user in the usual way, with the index and middle fingers grasping the flange 30 provided at the second end of the hollow body 2. The entire procedure, from the initial depression of the plunger 5 through to retraction of the needle 3 into the hollow barrel 2 following use, can be carried out with one hand, without changing the grip on the needle 3, thus providing a simple, safe process.

The retractable syringe of a second preferred embodiment is depicted in FIGS. 18 to 24. Features of the second embodiment which are equivalent to those of the first embodiment have been numbered similarly with the addition of 100 to the relevant reference numerals. This syringe operates in the same way as that of the first embodiment, but has been modified in the region of the hollow barrel first end 104 to more rigidly secure the needle 103 and to reduce the void at the hollow barrel first end 104 when the plunger 105 is depressed, thereby reducing the amount of fluid remaining in the hollow barrel 102 upon full depression of the plunger 105 during dispensing of the fluid.

Figure 18:
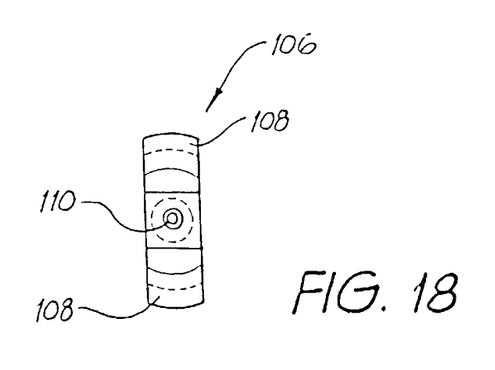
FIG. 18 is a view similar to FIG. 5 but depicting an end view of the needle of the retractable syringe of a second preferred embodiment.
Figure 19:
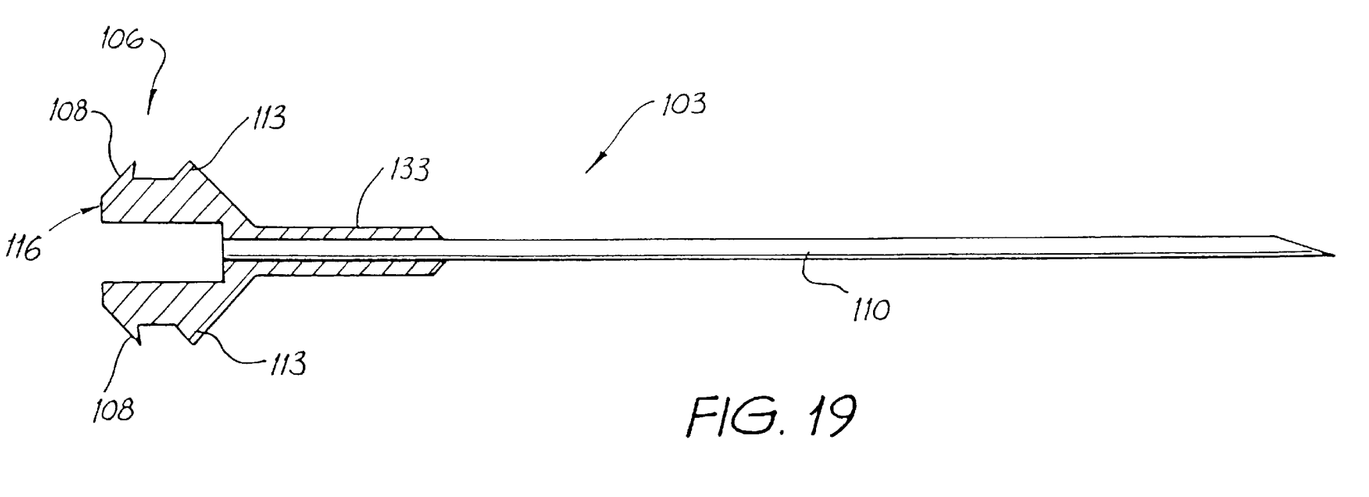
FIG. 19 is a view similar to FIG. 6 but depicting an elevation view of the needle of FIG. 18.

The modified needle 103, depicted in FIGS. 18 and 19, has a sleeve 133 disposed about the needle shaft 110 and extending from the needle interlocking portions 106. This sleeve 133 supports the needle 103 in the longitudinally extending aperture 125 of the hollow barrel first end 104. Accordingly, the longitudinally extending aperture 125 of this second embodiment is of a larger diameter than that of the first embodiment to receive the sleeve 133. The hole 124 radially extending across the longitudinally extending aperture 125 for reception of the circlip is also enlarged a corresponding amount, as is the protruding portion of the circlip (not depicted in enlarged modified form). The sleeve 133 is here integrally formed with the needle interlocking portions 106. The arrangement incorporating the sleeve 133 provides for a more rigid coupling between the needle 103 and the hollow barrel 102.

Figure 20:
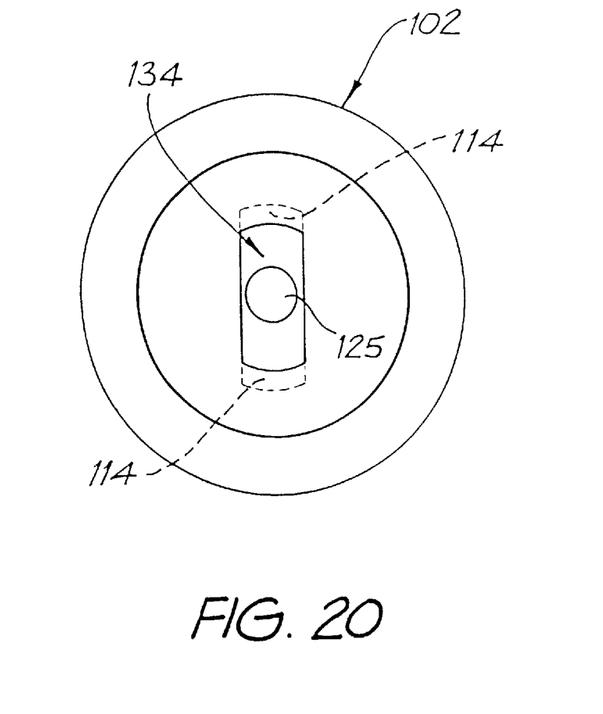
FIG. 20 is a cross sectional end view of the hollow barrel of the retractable syringe of the second preferred embodiment.
Figure 21:
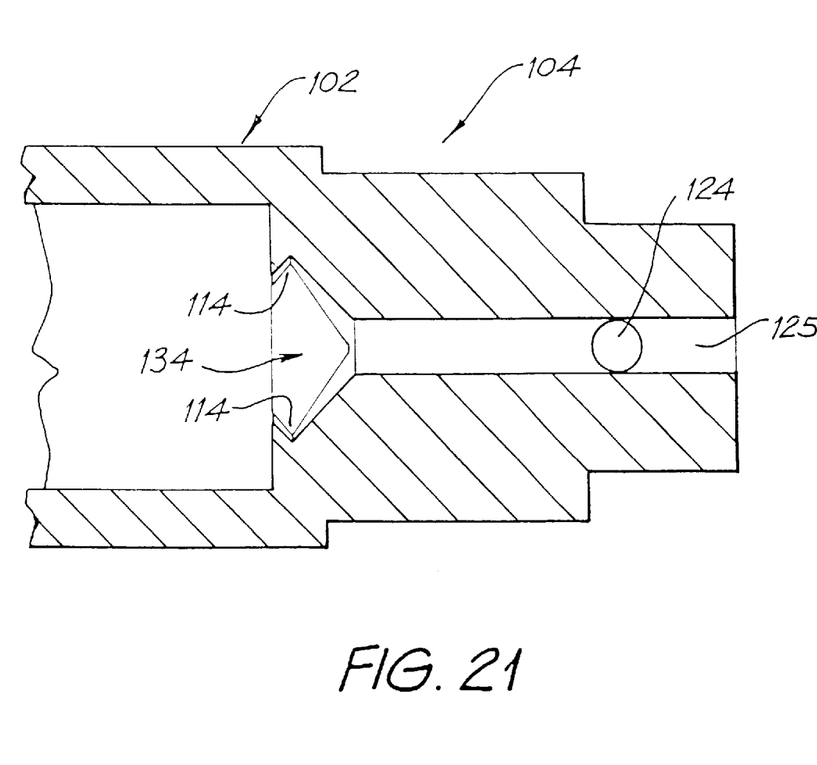
FIG. 21 is a view similar to FIG. 9 but depicting a fragmentary cross-sectional elevation view of the first end of the hollow barrel of FIG. 20.

The arrangement of the grooves 114 in the hollow barrel first end which cooperate with the triangular prism type projections 113 of the needle interlocking portions 116 to secure the needle 103 in the hollow barrel first end 104 has also been modified, as depicted in FIGS. 20 and 21. Whilst the grooves 14 of the first embodiment were formed as a continuous groove about the periphery of a conical recess in the hollow barrel first end, the second embodiment is arranged with the sides of the conical recess filled in so as to form a narrow recess 134 having a width corresponding to that of the needle interlocking portions 106 such that the needle interlocking portions 106 fit snugly into the recess 134 without a large void to either side. The grooves 114 are formed at opposing ends of the narrow recess 134 for engaging the triangular prism type projections 113 of the needle interlocking portions 106. This arrangement will also ensure the needle 103 is always installed in the correct orientation.

Figure 22:
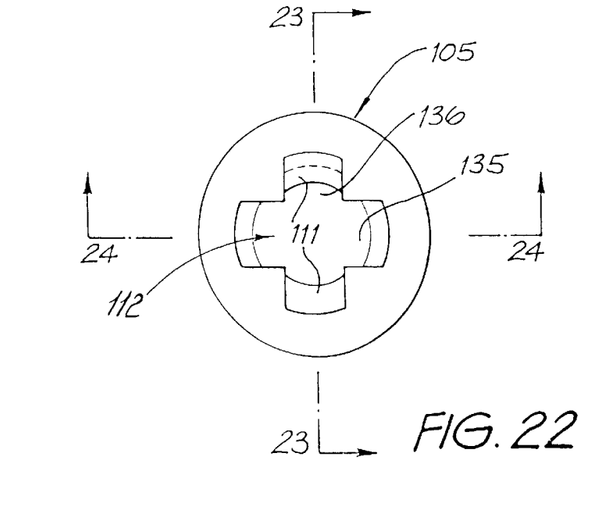
FIG. 22 is a view similar to FIG. 8 but depicting an end elevation view of the plunger of the retractable syringe of the second preferred embodiment.
Figure 23:
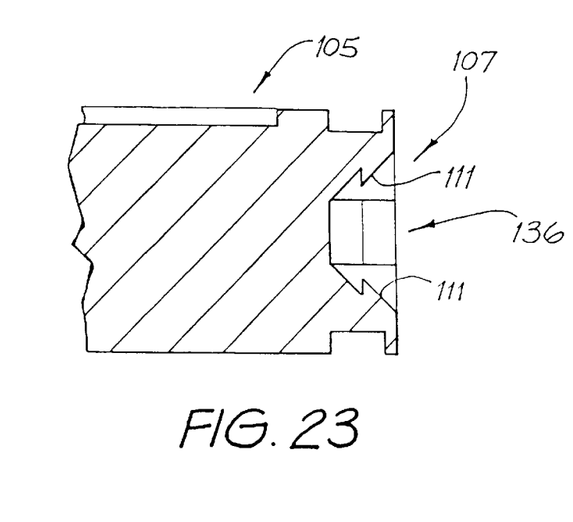
FIG. 23 is a view similar to FIG. 7 but depicting a fragmentary cross-sectional elevation view of the end of the plunger of FIG. 22 at section 23—23.
Figure 24:
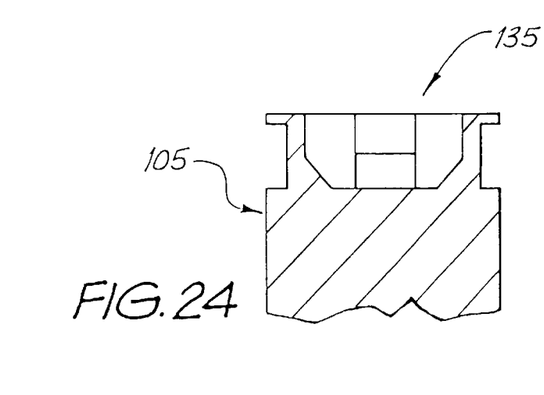
FIG. 24 is a fragmentary cross-sectional elevation view of the end of the plunger of FIG. 22 at section 24—24.

The end of the plunger 105 housing the plunger interlocking portion 107 according to the second embodiment has also been modified as depicted in FIGS. 22 to 24 to reduce the amount of void space in the recess 112 provided in the end of the plunger 105. The plunger interlocking portion 107 is again in the form of tabs 111 projecting inwardly from opposing sides of the recess 112 in a similar to that of the first embodiment. The general form of the recess 112, however is of first and second cavities 135, 136 intersecting at right angles, rather than the generally conical recess 12 of the first embodiment. On the initial depression of the plunger, the plunger recess 112 passes over the needle interlocking portions 106 such that they are aligned with the first cavity 135 so as not to engage the tabs 111. On the subsequent depression of the plunger 105 to dispense fluid and the associated rotation of the plunger through 90°, the needle interlocking portions 106 are aligned with the second cavity 136 enabling the tabs 111 to interlock with the needle barbs 108 of the needle interlocking portions 106. This modified arrangement wherein the recess 112 is largely filled in except for the two intersecting cavities 135, 136 also reduces the void in the hollow barrel when the plunger 105 is fully expressed so as to reduce the amount of fluid which is not dispensed.

We claim:

1. A single use retractable syringe comprising:
   a hollow barrel;
   a needle, engaged in a first end of said hollow barrel, fitted with a first locking portion;
   a plunger, slideably disposed in said hollow barrel, fitted with a second locking portion and provided with first and second slots; and a projection fixed relative to said hollow barrel and projected into one of said first and second slots provided on said plunger wherein said first and second correspond to lock portions locking at a particular relative angular position, said first slot orienting the plunger and the locking portions at other than the particular angular position, and said second slot orienting the plunger and the locking portions at the particular angular position;

the first slot deviates circumferentially around the plunger to meet the second slot; and the projection is positioned to pass from the first slot to the second slot on retraction of the plunger.

2. The single use syringe of claim 1 wherein said second slot extends substantially straight parallel to a longitudinal axis of said plunger, said first slot extending substantially straight parallel to said second slot from an end of said plunger opposed to said hollow barrel first end to partway along said plunger where said first slot deviates circumferentially to intersect with said second slot.

3. The single use retractable syringe of claim 2 wherein said projection is formed on a cap mounted on a second end of said hollow barrel opposed to said first end.

4. The single use syringe of claim 1 wherein said first and second slots are located to rotate said plunger through approximately 90° on retraction of the plunger.

5. The single use retractable syringe of claim 1 including a clip having a protruding portion, said protruding portion abutting said needle and said clip being biased such that, on retraction of said needle into said hollow barrel, said protruding portion moves to block off an aperture vacated by said retracting needle.

6. The single use syringe of claim 1 wherein said plunger is spring biased to a retracted position.

* * * * *